(12) United States Patent
Watson

(10) Patent No.: US 6,443,729 B1
(45) Date of Patent: Sep. 3, 2002

(54) ILLUMINATED DENTAL MIRROR

(76) Inventor: Jeffrey A. Watson, 5023 Pine Valley Dr., Fayetteville, NY (US) 13066

( * ) Notice: Subject to any disclaimer, the term of this patent is extended or adjusted under 35 U.S.C. 154(b) by 0 days.

(21) Appl. No.: 09/821,310

(22) Filed: Mar. 29, 2001

(51) Int. Cl.⁷ .............................. A61B 1/24
(52) U.S. Cl. ..................... 433/30; 433/29; 433/31; 433/116
(58) Field of Search ................ 433/29, 30, 31, 433/32, 116; 600/247, 248

(56) References Cited

U.S. PATENT DOCUMENTS

| | | | |
|---|---|---|---|
| 3,634,938 A | 1/1972 | Hutchinson | 433/29 |
| 3,638,013 A | 1/1972 | Keller | 433/31 |
| 3,969,824 A | 7/1976 | Widen et al. | 433/30 |
| 3,986,266 A | 10/1976 | Vellender | 42/69 |
| 4,279,594 A | 7/1981 | Rigutto | 433/31 |
| 4,334,863 A | 6/1982 | Magid et al. | 433/29 |
| 4,477,252 A | 10/1984 | Lieb et al. | 433/29 |
| 4,629,425 A | 12/1986 | Detsch | 433/31 |
| 4,795,343 A * | 1/1989 | Choisser | 433/116 |
| 4,810,194 A * | 3/1989 | Snedden | 433/116 |
| 4,925,391 A | 5/1990 | Berlin | 433/31 |
| 4,993,945 A | 2/1991 | Kimmelman et al. | 433/30 |
| 5,139,420 A | 8/1992 | Walker | 433/31 |
| 5,139,421 A | 8/1992 | Verderber | 433/31 |
| 5,267,860 A * | 12/1993 | Ingram, Jr. et al. | 433/116 |
| 5,295,826 A | 3/1994 | Yandell et al. | 433/31 |
| 5,385,468 A | 1/1995 | Verderber | 433/77 |
| 5,449,290 A | 9/1995 | Reitz | 433/31 |
| 5,457,611 A | 10/1995 | Verderber | 362/32 |
| 5,921,776 A * | 7/1999 | Heilbrunn | 433/116 |
| 5,951,284 A * | 9/1999 | Lake | 433/31 |

OTHER PUBLICATIONS

Welch–Allyn—DenLite Instruction Manual.
Welch–Allyn—DenLite Product Literature.

* cited by examiner

Primary Examiner—Cary E. O'Connor
(74) Attorney, Agent, or Firm—Lawrence P. Trapani

(57) ABSTRACT

A dental mirror comprising a handle, a mirror, a tubular member inside the handle, a light source inside the tubular member, a light transmitting element coupled to the light source, a thermally conductive fluid conduit coiled around the tubular member, a fluid discharge manifold, a manifold support member for supporting the manifold adjacent to the mirror, a first connector attached to one end of the handle, a second connector attached to the first connector, and a combined electric/air supply line coupled to the second connector. The supply line couples electrical energy and compressed air to the handle via the connectors. The compressed air is coupled to the fluid conduit to aid in cooling the handle while the light source is energized. The air, having been warmed during the cooling process, is then channeled to the mirror to clean and defog the mirror.

13 Claims, 6 Drawing Sheets

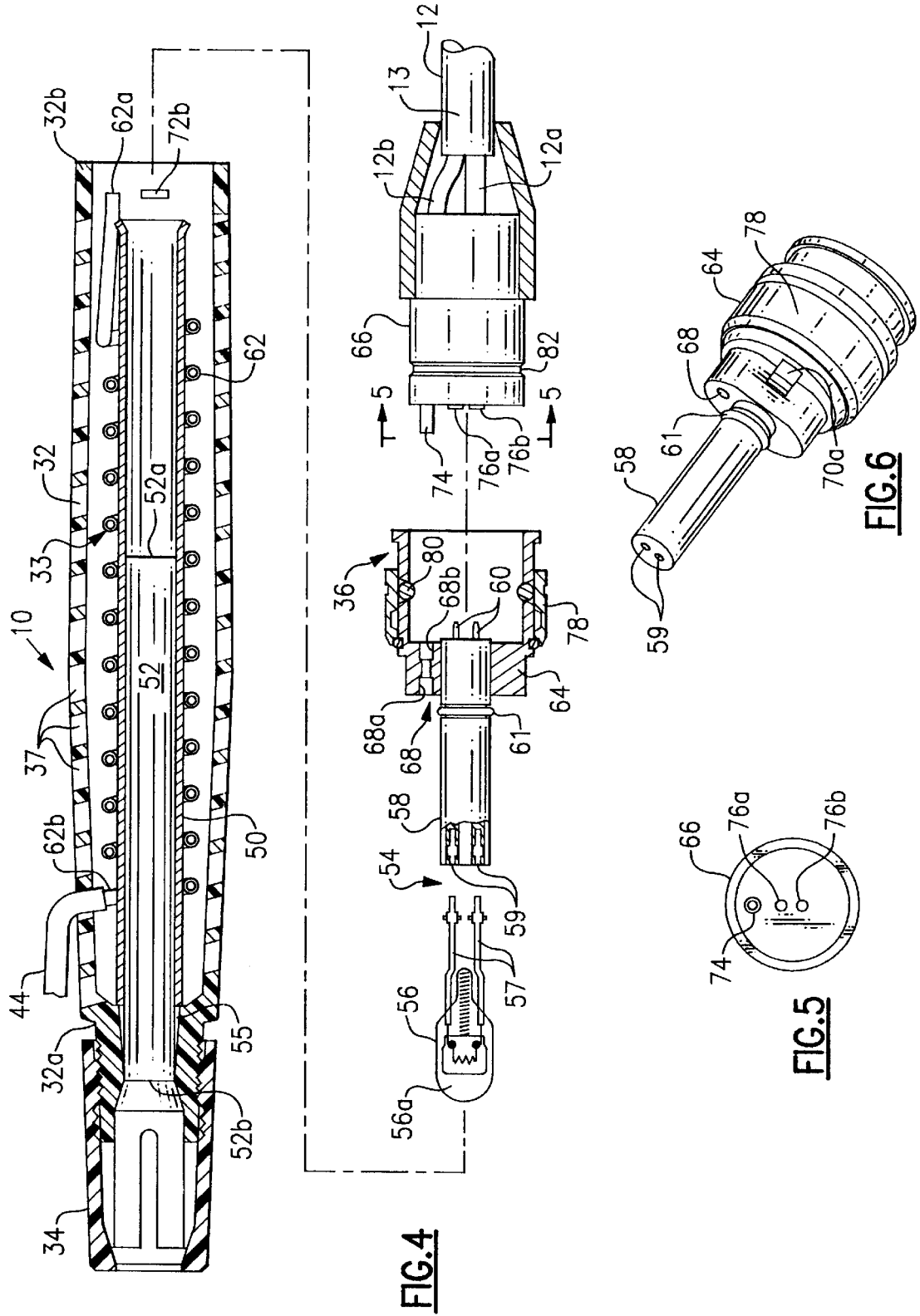

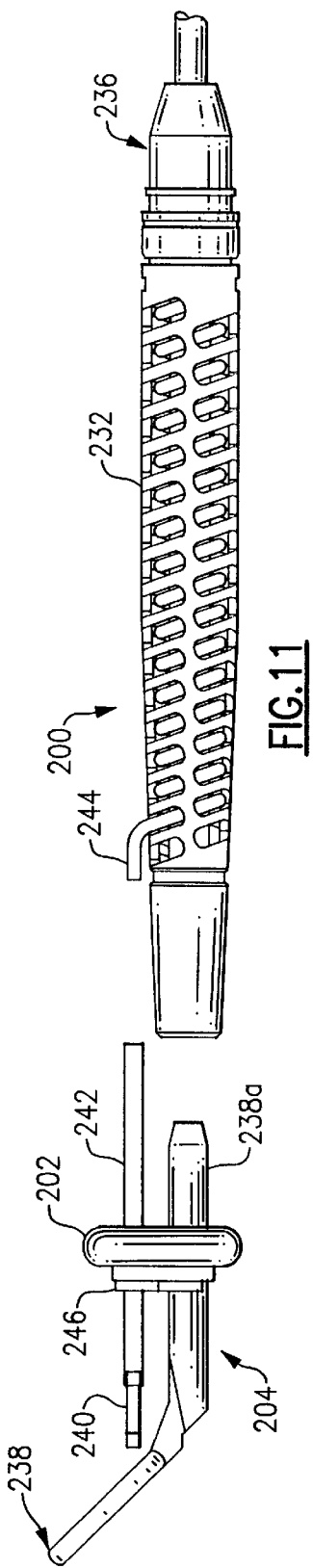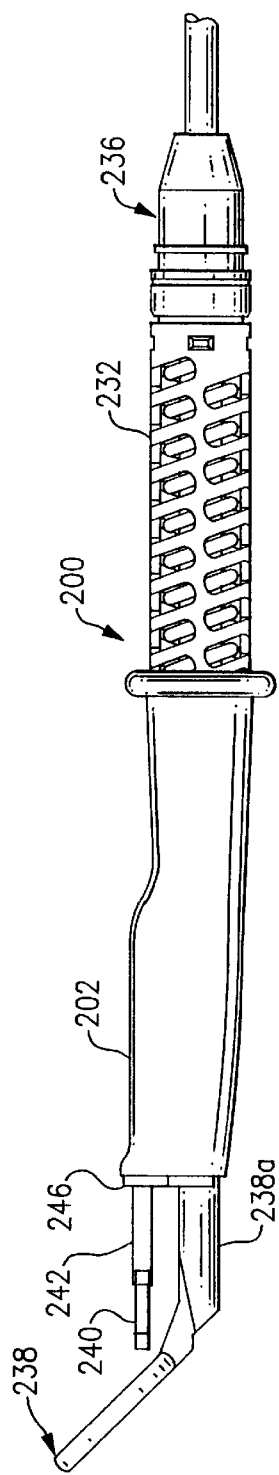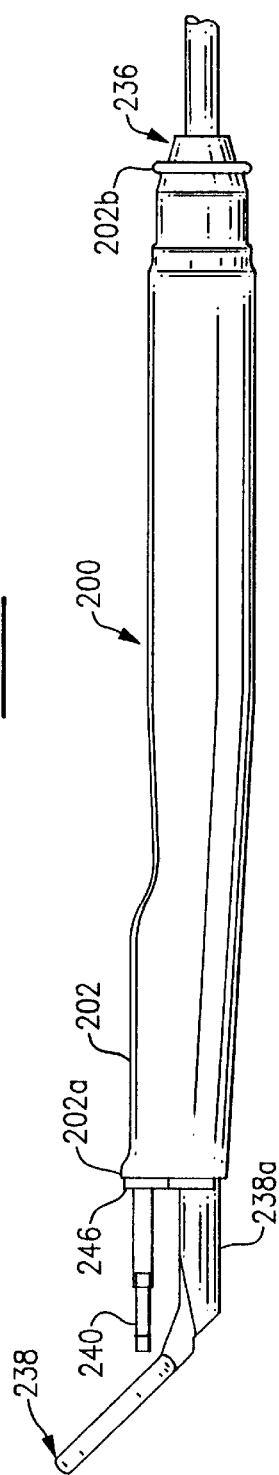

ILLUMINATED DENTAL MIRROR

BACKGROUND OF THE INVENTION

1. Technical Field

The present invention relates generally to hand-held dental instruments, and more particularly to hand-held dental mirrors which are illuminated by fiber optic light sources.

2. Background Art

The dental mirror has long been and continues to be a prolific instrument in the clinical fields of dentistry. In the last 30 years, the dental industry has sought to develop a mirror with its own illumination system. Examples of such mirrors are disclosed in U.S. Pat. Nos.: 3,638,013 to Keller; 4,279,594 to Rigutto; 4,629,425 to Detsch; 4,993,945 to Kimmelman et al.; 5,139,420 to Walker; 5,139,421 to Verderber; and 5,457,611 to Verderber. The most successful of these mirrors have been those which contain a light source built in the handle of the mirror. The mirror disclosed in U.S. Pat. No. 5,457,611 to Verderber is such a device; it is the only known illuminated mirror that has been succesfully marketed. The Verderber mirror is currently produced and marketed by Welch-Allyn, Inc., of Skaneateles, N.Y.

The problem with illuminated mirrors having built-in light sources is that the handle or handpiece supporting the mirror heats up to a temperature that is uncomfortable to the user. As a result, the user (e.g., a dental clinician) may have a tendency to put the mirror down repeatedly during clinical procedures. Also, the clinician may be inclined to alternate mirrors during longer procedures to avoid the discomfort. These practices invariably prolong procedures, distract the clinician, and compromise accuracy, all to the detriment of the patient.

A solution to the heat problem is proposed in U.S. Pat. No. 5,457,611 to Verderber. In Verderber, a high intensity lamp is contained in a heat sink mounted within the dental mirror handle. The handle contains multiple vents spaced from and surrounding the heat sink. Heat from the lamp radiates out through the vents from the heat sink. This convection creates a thermal current, causing heated air to exhaust through the vents and be replaced by cooler air from the surrounding atmosphere (hereinafter referred to as "ambient cooling"). Even with the aid of ambient cooling, the heat generated by the lamp becomes particularly noticeable within 15 minutes. Handle temperatures for the Verderber mirror have reached 134° F., which are uncomfortable and distracting to the clinician.

Another approach to cooling a dental handpiece is disclosed in U.S. Pat. Nos.: 4,334,863 to Magid et al.; 4,477,252 to Lieb et al. and 3,634,938 to Hutchinson. Magid et al. discloses cooling the lamp, in part, by passing water and air through parallel channels adjacent to the lamp (FIG. 4). This approach is not sufficient by itself to prevent the handpiece from becoming uncomfortably hot—a critically dimensioned air gap and shield are also required. Lieb et al. discloses cooling the lamp (FIGS. 4 and 6) with exhaust air from a turbine drill; the exhaust air passes adjacent to and around the lamp.

In Hutchinson, cooling is accomplished by a water coil around the lamp (FIG. 3) and an air circulating chamber; water and air used for operating a turbine drill is passed through the coil and chamber, respectively, to effect the cooling. None of these approaches are particularly suitable for improving or retrofitting with the commercially produced dental mirror disclosed in U.S. Pat. No. 5,457,611 to Verderber.

A longstanding shortcoming inherent in a dental mirror is the tendency of the reflective surface to become obscured during clinical procedures. Fog, mist, spray from dental drills, tooth debris, dental materials, etc., collect on the mirror's reflective surface, impairing the visibility of the image from the mirror. The need for clear mirrors in dental and otolaryngology offices is immense. The affected procedures range from hygiene procedures (which are an important and constant activity in the dental office) to extensive oral surgeries as well as medical office examinations.

Clinicians are forced to repeatedly clean or wipe the reflective surface, which requires repositioning of the mirror. This repeated repositioning, however, can disrupt the concentration of the clinician, leading to reduced accuracy. Furthermore, much time is lost by the clinician in removing the mirror from the patient's mouth, cleaning or wiping the surface, then repositioning the mirror in order to continue with the procedure.

As a result of all of this, some clinicians opt not to use a dental mirror at all. Instead, they position the patient at an angle that allows for a more clear and direct view of the procedure. However, the clinicians must awkwardly position their heads, necks and backs to achieve such a view. Discomfort and strain are often experienced by both the clinician and the patient. Clinicians may develop temporary or even permanent neck and back problems as a result of such practices.

Attempts have been made to automatically clear (or "self-clean") the mirror with a flow of air and/or water. Examples of such attempts are disclosed in U.S. Pat. Nos.: 5,449,290 to Reitz; 5,139,420 to Walker; 4,925,391 to Berlin; 4,629,425 to Detsch; 4,279,594 to Rigutto; and 3,969,824 to Widen et al. The mirrors disclosed in these patents do not contain a light source in the handle; and thus, there is no suggestion that the air and/or water used to clean the mirror may also be used to cool the handle. In addition, there is no coincidental warming of the air/water by an onboard light source before the air/water is applied to the mirror. While these self-cleaning approaches are theoretically sound, they have not, to this inventor's knowledge, been commercially successful. Further, there is no suggestion that such approaches be especially adapted for the commercially produced dental mirror disclosed in U.S. Pat. No. 5,457,611 to Verderber. Verderber discloses no provision for self-cleaning or defogging the mirror.

Another problem with dental mirrors is that their reflective surfaces are susceptible to marring by tooth debris, dental materials, or aluminum oxide powder from air-abrasion systems. When such marring occurs, the mirror must be replaced. This adds to the cost of treating a patient, which cost is passed on to the patient. In self-cleaning systems using a flow of water, the mirror is coincidentally protected from abrasion, to some degree, by the water; however, water, as a protection mechanism, creates two new problems—(1) distortion of the image from the mirror, and (2) the need to evacuate the water.

In some situations, it may be desirable or necessary to quickly replace the handle of an illuminated dental mirror during a procedure (e.g., if the lamp burns out or some other electrical malfunction occurs). As disclosed in U.S. Pat. No. 5,457,611 to Verderber, the handle of the mirror is connected to an electrical cord which supplies electrical power to the lamp. In order to separate the handle from the cord, a rear end cap must be unsnapped (FIG. 2) or unscrewed (FIG. 5) from the body of the handle. Such separation mechanisms are not expedient when a quick handle replacement is necessary during a clinical procedure.

A further problem with dental mirrors is the risk of transmitting germs from one patient to another (i.e., "cross contamination"). Cross contamination is possible because the handle of the mirror is exposed to the patient during clinical procedures. The recommended approach for preventing cross contamination is to autoclave the mirror handle after each use. Such an approach is time consuming and requires access to and handling of autoclave equipment and materials. Further, the autoclave process increases the wear-and-tear on the mirror handle.

OBJECTS AND SUMMARY OF THE INVENTION

It is therefore an object of the present invention to provide display apparatus and methods that avoid the limits and problems associated with the prior art.

It is another object of the present invention to maintain the temperature of a dental handpiece, containing a light source, at comfortable levels during clinical procedures.

It is a further object of the present invention to improve upon the dental mirror disclosed in U.S. Pat. No. 5,457,611 to Verderber.

It is yet another object of the present invention to provide certain retrofittable components for the dental mirror of U.S. Pat. No. 5,457,611.

It is yet a further object of the present invention to provide a self-cleaning and self-defogging dental mirror.

It is still another object of the present invention to cool a dental handpiece, containing a light source, using compressed air from a standard dental office air-supply.

It is still a further object of the present invention to utilize the compressed air, after it has been warmed during the cooling process, to also clean and defog the mirror.

It is yet still another object of the present invention to reduce marring of the reflective surface of the dental mirror by directing the compressed air onto the reflective surface in a fan-like pattern.

It is yet still a further object of the present invention to provide an expedient means for interchanging dental mirror handles.

It is yet still a further object of the present invention to effectively eliminate the risk of cross-contamination associated with the use of dental mirrors.

These and other objects are attained in accordance with the present invention wherein there is provided an illuminated dental mirror instrument comprising a handle, a mirror, an elongated tubular member, an electric light source, a light transmitting element, a thermally conductive fluid conduit, a fluid discharge manifold, a manifold support member, first and second complementary connectors, and a combined electrical and fluid supply line.

The handle of the instrument is defined as having front and rear ends. The mirror contains a reflective surface and includes a shank portion which is releasably attached to the front end of the handle. The elongated tubular member is located within the handle. The light source is contained within the elongated tubular member. The light transmitting element transmits light from the light source to the front end of the handle. The thermally conductive fluid conduit is coiled around the elongated tubular member, and the conduit is defined as having an intake end and a discharge end.

The fluid discharge manifold of the instrument is coupled to the discharge end of the fluid conduit via a fluid tube. The manifold support member is removably secured to the shank of the mirror and supports the manifold adjacent to the reflective surface of the mirror. The fluid tube is supported by the support member. The manifold is configured to discharge fluid in a fan-like pattern over the reflective surface of the mirror.

The first connector of the instrument is removably connected to the rear end of the handle, and it contains a fluid passage removably coupled to the intake end of the fluid conduit. The light source is mounted to the first connector.

The second connector of the instrument is removably connected to and mates with the first connector. The second connector contains a fluid passage removably coupled to the fluid passage of the first connector. The second connector includes electrical conductors which are removably electrically coupled to the light source.

The combined electric and fluid supply line is coupled to the second connector and serves to couple electrical energy and fluid to the electrical conductors and fluid passage, respectively, of the second connector.

In another aspect of the present invention, there is provided a method of retrofitting a dental mirror instrument. The instrument is of the type having: (i) a handle containing a plurality of vents; (ii) a mirror with a reflective surface coupled to the handle; (iii) an elongated tubular member located within the handle; (iv) an electric light source contained within the elongated tubular member; (v) a light transmitting element for transmitting light from the light source to the mirror; (vi) an end cap removably attached to the handle; and (vii) an electrical cord, secured to the end cap, which includes a pair of wires coupled to the light source.

The method of retrofitting the instrument comprises the steps of: (a) removing the light source, end cap and electrical cord from the handle; (b) removing the elongated tubular member from the handle; (c) placing a thermally conductive, helical-shaped, fluid conduit around the elongated tubular member to create a subassembly, the fluid conduit having an intake end and a discharge end; (d) installing the subassembly in the handle, such that the discharge end of the fluid conduit is accessible through a vent in the handle; (e) coupling a fluid discharge manifold to the discharge end of the fluid conduit; (f) attaching a support member to the instrument and using the member to support the discharge manifold adjacent to the reflective surface of the mirror; (g) replacing the light source, end cap, and electrical cord of the instrument with a replacement light source, first and second connectors, and a supply line, the replacement light source being mounted to the first connector and the supply line being mounted to the second connector; (h) inserting the replacement light source into the elongated tubular member; (i) connecting the first connector to the handle, in place of the end cap; and (j) connecting the second connector to the first connector.

In a further aspect of the present invention, a protective contaminant-resistant sheath assembly for a dental instrument is provided. The assembly comprises a support and an elongated protective sheath. The support is adapted to be coupled to the dental instrument. The protective sheath is made from a flexible contaminant-resistant material. The sheath has a first end secured to the support and a second end. The second end is open and free to allow manual deployment of the sheath over and around at least a portion of the dental instrument.

BRIEF DESCRIPTION OF THE DRAWING

Further objects of the present invention will become apparent from the following description of the preferred embodiment with reference to the accompanying drawing, in which:

FIG. 4 is an enlarged exploded view, in partial section, of a handpiece for the illuminated dental mirror of the present invention;

FIG. 5 is an elevation view, along line 5—5 in FIG. 4, of a male connector of a quick-disconnect coupler, which coupler forms part of the handpiece of FIG. 4;

FIG. 6 is a perspective view of a female connector of the quick-disconnect coupler and a lamp socket attached thereto;

FIG. 11 is a side elevation view of the illuminated dental mirror of the present invention, employing a protective sheath, which is shown in an undeployed position;

FIG. 12 is a side elevation view of the illuminated dental mirror of FIG. 11, showing the protective sheath in a partially deployed position; and FIG. 13 is a side elevation view of the illuminated dental mirror of FIG. 11, showing the protective sheath in a fully deployed position.

DETAILED DESCRIPTION OF THE PREFERRED EMBODIMENT

Figure 1:
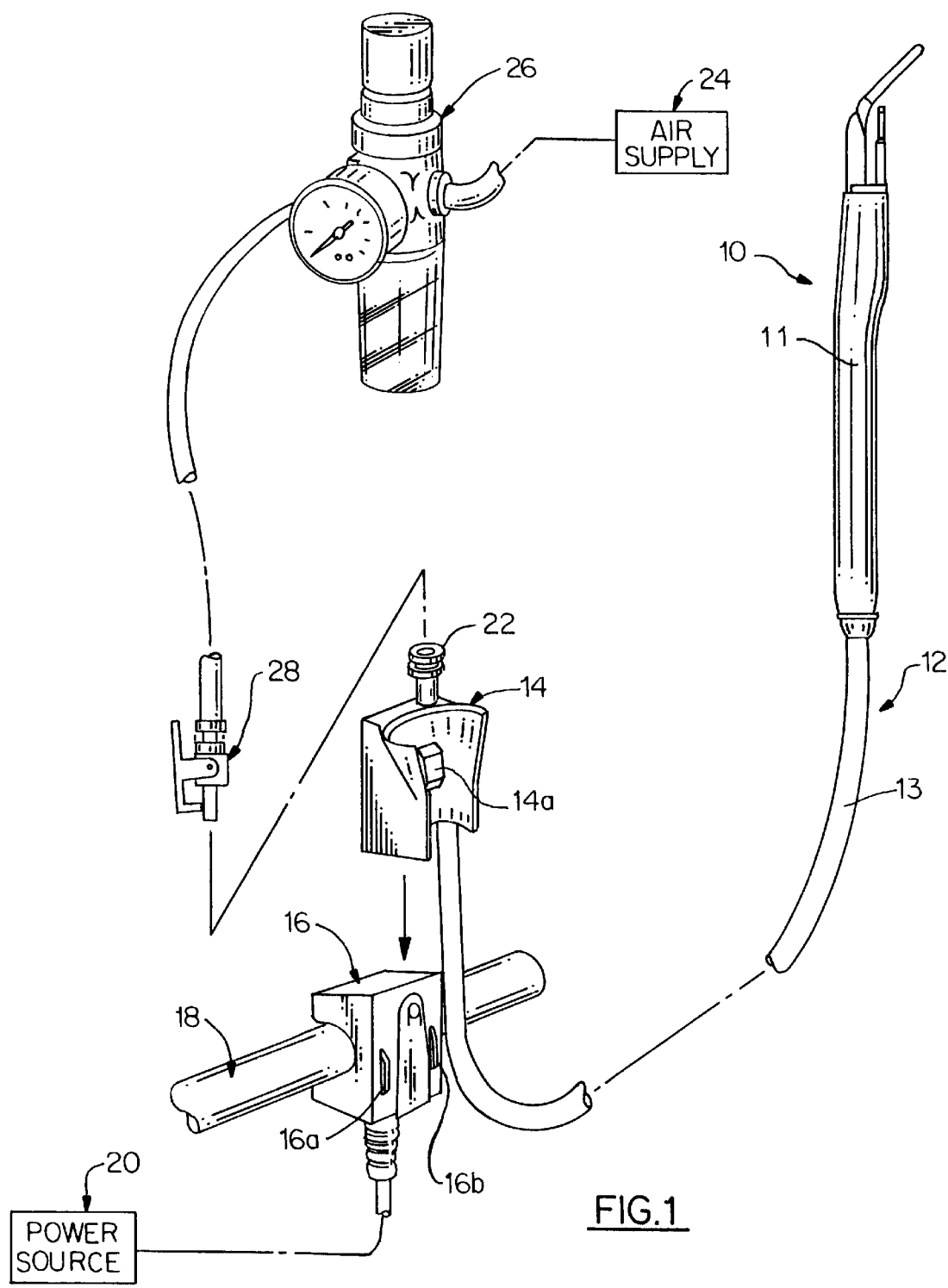
FIG. 1 is a perspective view of an illuminated dental mirror with associated components, constructed in accordance with the present invention.

Referring to FIG. 1, there is shown an illuminated dental mirror instrument 10 constructed in accordance with the present invention. Instrument 10 is shown with an optional protective sheath 11 covering most of the instrument. As will be described in detail below, electrical energy and compressed air are supplied to instrument 10 via a supply line 12. Supply line 12 contains, within an outer casing 13, an electrical cord 12a and a compressed air line 12b (FIG. 4). Supply line 12 is coupled to an instrument holder 14. Holder 14 is suitably configured to releasably hold instrument 10.

As shown in FIG. 1, holder 14 is configured to be removably secured to a mounting block 16. Block 16 is mounted on a suitable support structure 18. An electrical power supply 20 supplies electrical energy to mounting block 16. Holder 14 and block 16 each contain a pair of electrical contacts. The contacts of block 16 (16a, 16b) are in physical contact with the contacts of holder 14 (not shown) when block 16 and holder 14 are secured together. The electrical energy from power source 20 is coupled to instrument 10 via the assembly comprising block 16, holder 14, and electrical cord 12a. The construction and electrical operation of the assembly is well known and fully described in U.S. Pat. No. 5,385,468 to Verderber ("Verderber I"), which is incorporated herein by reference.

In accordance with the present invention, instrument holder 14 (FIG. 1) has been modified from what is shown in Verderber I. Holder 14 includes a compressed air fitting 22 which is directly coupled to and in fluid communication with (not shown) the compressed air line in supply line 12. A typical dental office air supply 24 can be coupled to fitting 22 to provide compressed air to instrument 10. As suggested in FIG. 1, a compressed air filter/regulator 26 may be inserted between air supply 24 and fitting 22 to remove most liquids and solid particles from the air and regulate air pressure to instrument 10. The preferred air pressure level to be delivered to instrument 10 is about 40–60 PSI. A quick-disconnect connector 28 is used to connect the filtered and regulated air supply to fitting 22.

A manual shutoff valve (not shown) may also be included between filter/regulator 26 and fitting 22. In an alternative implementation, an automatic shutoff valve may be employed inside holder 14. As described in Verderber I, an electrical switch contact (14a in my FIG. 1) is located on holder 14. Switch contact 14a functions to turn off the electric power to instrument 10 when the instrument is held in holder 14, and to turn on the electric power when instrument 10 is removed from holder 14. This same electrical switch can be employed for turning on and shutting off the compressed air. Swith contact 14a can be used with an electrically powered automatic shutoff valve (e.g., a solenoid actuated valve) located in holder 14, for the compressed air.

Figure 2:
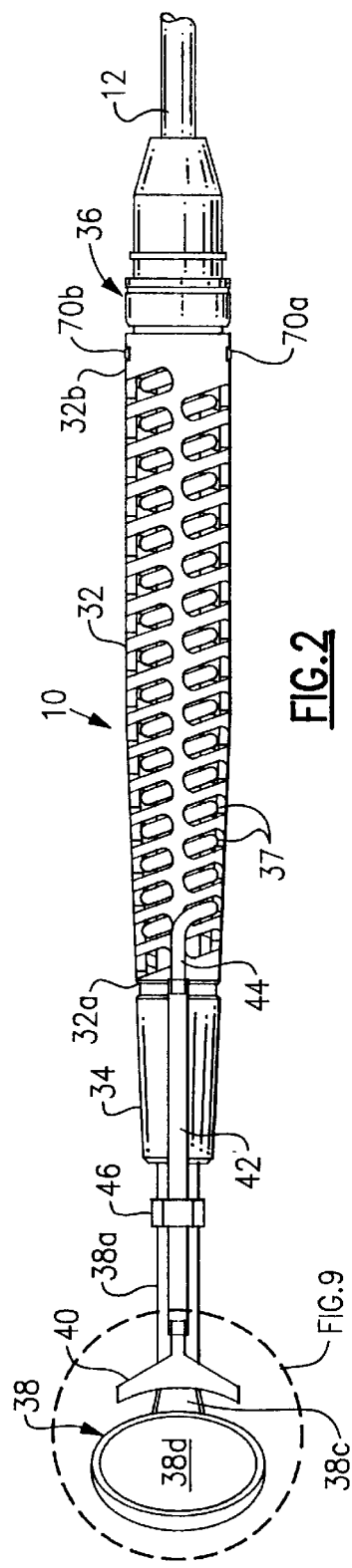
FIG. 2 is a top plan view of the illuminated dental mirror of the present invention, shown without a protective sheath.
Figure 3:
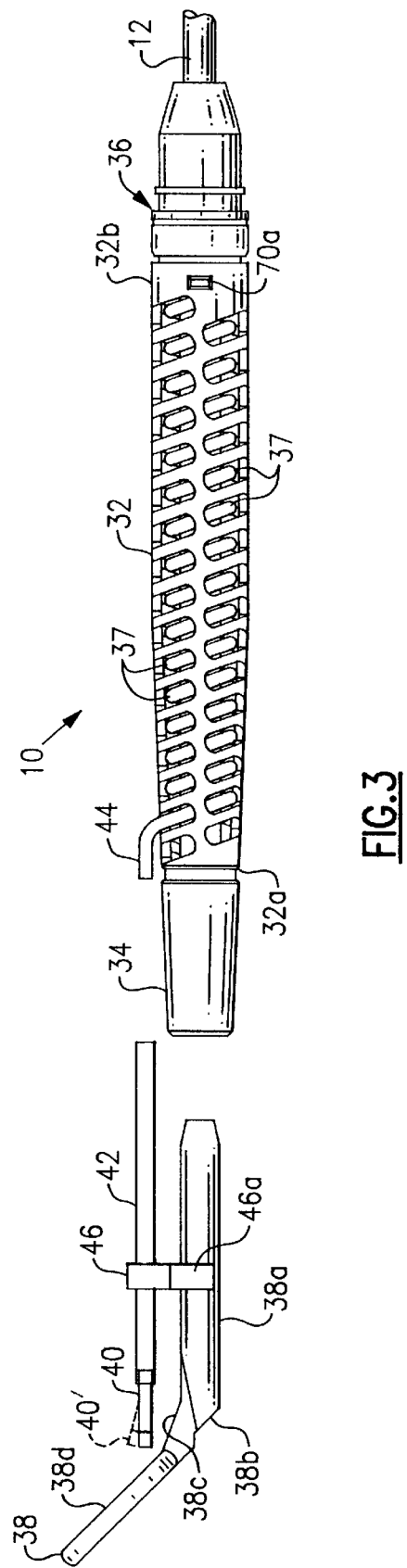
FIG. 3 is a side elevation view of the illuminated dental mirror of FIG. 2, shown with the mirror and associated components detached.

Referring now to FIGS. 2–4, the construction of instrument 10 will now be more fully described. Instrument 10 is a modification of an existing dental instrument disclosed in U.S. Pat. No. 5,457,611 to Verderber ("Verderber II"), which is incorporated herein by reference. Familiarity with Verderber II is assumed in the following description of instrument 10. Instrument 10 includes a handle 32 having a front end 32a and a rear end 32b. A front cap 34 is threaded onto front end 32a (FIG. 4), and a quick-disconnect coupler 36 is removably attached to rear end 32b. The downstream end of supply line 12 is connected to coupler 36 to supply compressed air and electricity to instrument 10. 32 Handle 32, cap 34, and coupler 36 are preferably made of low heat absorbing material.

Handle 32 contains a plurality of air vents 37 through the wall of handle 32, which allows ambient air to circulate in and out of the handle. The wall of handle 32 defines an interior volume 33 (FIG. 4). A mirror 38 is inserted into front cap 34 and is secured in place by tightening cap 34 on the threaded portion of handle 32. This securement mechanism is more fully explained in Verderber II. Mirror 38 includes a shank portion 38a, a heel portion 38b, a face portion 38c, and a reflective surface 38d. Mirror 38 is a fiber optic disposable mirror of the type in which light transmitted into shank portion 38a is emitted from heel portion 38b and face portion 38c. Such a mirror is commercially available and supplied by Welch-Allyn, Inc. Skaneateles, N.Y.

With further reference to FIGS. 2–4, instrument 10 contains an air discharge manifold 40 connected to an air tube 42 which is, in turn, connected to a flexible connector hose 44. A support member 46 (see also FIG. 8) is removably secured to mirror shank 38a. Support member 46 may be configured as a clip-on or slip-on device, where an engagement portion 46a (FIG. 8) is either open to clip onto or closed to slip onto the mirror shank. Support member 46 contains a hole 46b through which air tube 42 passes, and air tube 42 is supported thereby. Air tube 42 is preferably firm enough to support manifold 40 adjacent to reflective surface 38d of mirror 38. Manifold 40, air tube 42, connector hose 44, and support member 46 are all disposal parts, made of an inexpensive material. Manifold 40 and support 46 may be made from Delrin® material.

Figure 9:
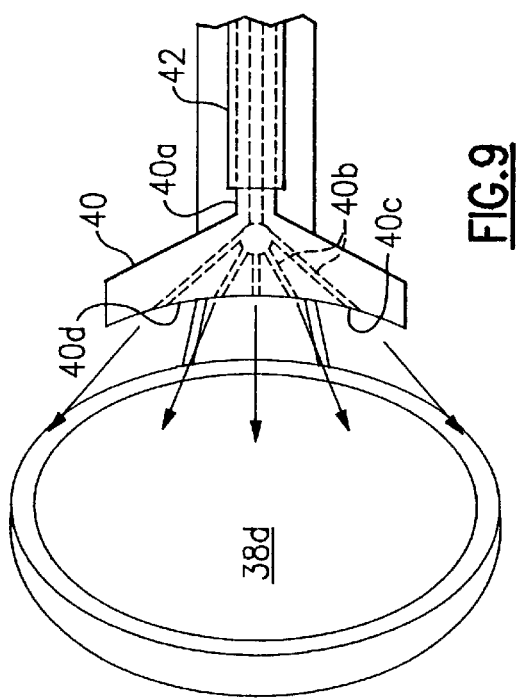
FIG. 9 is an enlarged fragmentary view of that portion of the illuminated dental mirror of FIG. 2, that is encircled by a dashed line in FIG. 2.

As shown in FIG. 9, an intake port 40a of manifold 40 is inserted into air tube 42, to make the fluid connection thereto. In an alternative implementation, intake port 40a and air tube 42 are adapted so that air tube 42 can be inserted into intake port 40a. Also, on the other end of air tube 42, connector hose 44 may be eliminated if air tube 42 is flexible enough, at that end, to be inserted into the interior volume of handle 32.

As shown in FIG. 2, manifold 40 is positioned such that it does not completely block the light emitted from front face 38c of mirror 38. As shown in FIG. 9, manifold 40 is positioned above reflective surface 38d and discharges streams of air, in a fan-like pattern, down and over reflective surface 38d. Manifold 40 contains a plurality of air branch lines 40b and discharge openings 40c, respectively. Discharge openings 40c are contained in a front face 40d of manifold 40. Branch lines 40b converge into and are in fluid communication with intake port 40a.

In some cases, it may be desirable to alter the direction of the air streams from manifold 40 from what is shown in FIG. 9. It may be preferable to make the air streams geometrically normal to the curvature of the mirror. This can be accomplished, e.g., by reconfiguring manifold 40 and matching the curvature of face 40d with the curvature of mirror 38. Also, it may be preferable to aim face 40d of manifold 40 slightly "upward" (in the orientation shown in FIG. 3). The alternate position for manifold 40 is shown in phantom lines in FIG. 3, and is referenced by numeral 40'. In this alternate orientation, the air streams from manifold 40' are incident on reflective surface 38d at a more shallow angle. It is not desirable to make this angle zero (i.e., air streams parallel to reflective surface 38d).

The internal components of instrument 10 will now be described with reference to FIGS. 4–7. Again, familiarity with the disclosure in Verderber II is assumed in the following description. A heat sink 50, configured as an elongated tubular member, is contained within interior volume 33 of handle 32. Heat sink 50 is made of a thermally conductive material, such as aluminum or copper. A light transmission rod 52 is located within the front end of heat sink 50, and is secured therein by means of an adhesive or interference fit. Rod 52 may made of any material having a high light transmission capability, such high quality quartz glass.

A light source 54 is located within the rear end of heat sink 50. Light source 54 includes a high intensity halogen lamp 56 having a pair of leads 57 inserted into a lamp base or socket 58 (FIG. 4). Socket 58 includes a pair of electrical socket contacts 59 in which leads 57 are inserted. Socket 58 also includes a pair of electrical conductors or pins 60 electrically connected to contacts 59, respectively. Socket 58 contains an external circumferential groove in which an O-ring 61 or other elastomeric seal is seated. When light source 54 is inserted into heat sink 50, O-ring 61 is compressed by the interior wall of heat sink 50, effecting a moisture resistant seal.

Light source 54 is positioned within heat sink 50 at close proximity to a rear end 52a of rod 52, such that light emitted from lamp 56 is optically coupled into rod 52. Lamp 56 may also include a lens 56a for focusing light into end 52a. Light coupled into rod 52 is transmitted to a front end 52b of rod 52 and then optically coupled into mirror shank 38a.

The front end of heat sink 50 is secured in handle 32 by virtue of rod 52 closely engaging an inner surface 55 of end 32a of the handle. The rear end of heat sink 50 is secured by its engagement with O-ring 61 and socket 58. Of course, other well known securement or mounting approaches may me employed. The claimed invention is not limited to any particular approach.

In accordance with the present invention, a thermally conductive, helical-shaped, fluid conduit 62 is located around heat sink 50 (see FIGS. 4 and 5). Preferably, conduit 62 is made of thin-walled stainless steel and is in close contact with heat sink 50. Conduit 62 includes an intake end 62a and a discharge end 62b. Connector hose 44 is inserted into housing 32, through a vent 37, and slipped over discharge end 62b of conduit 62 (FIG. 4). Discharge end 62b is preferably slightly tapered to facilitate the union of hose 44 with the discharge end. From the description thus far, it understood that a complete fluid channel is established through conduit 62, connector hose 44, tube 42, and discharge manifold 40.

With further reference to FIGS. 4–6, quick-disconnect coupler 36 comprises a female connector 64 and a male connector 66. Light source 54 is rigidly mounted to female connector 64; however, in an alternative embodiment, light source 54 may be threaded into connector 64. Conductor pins 60 of light source 54 project into the interior of connector 64 (FIG. 4). In an alternative arrangement, connector 64 could be configured with its own pair of conductor pins, which would be, in turn, electrically coupled to light source 54. The claimed invention is not limited to any particular conductor pin approach.

Figure 7:
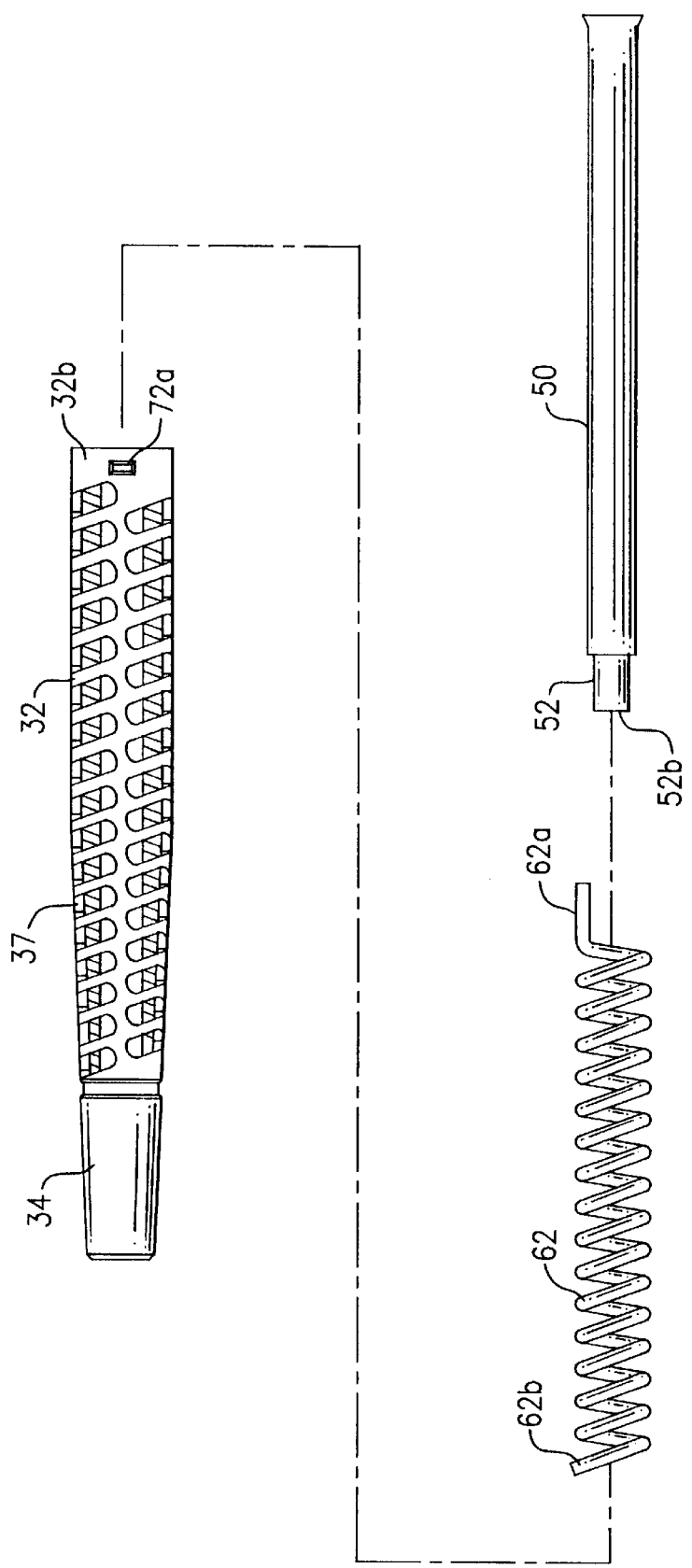
FIG. 7 is an exploded view of the handle portion of the handpiece of FIG. 4.

As shown in FIG. 4, female connector 64 contains a fluid passage 68 having a front coupling section 68a and a rear coupling section 68b. Connector 64 is removably attached to rear end 32b of handle 32. The removable attachment is established by means of a pair of resilient locking snaps 70a and 70b (see FIGS. 2 and 6) snapping into slots 72a and 72b, respectively. Female connector 64 is made resilient enough to allow manual depression of the connector to a sufficient degree to disengage snaps 70a and 70b from slots 72a (FIG. 4) and 72b (FIG. 7). When connector 64 is properly attached to handle 32, coupling section 68a of fluid passage 68 is coupled to intake end 62a of conduit 62.

With further reference to FIGS. 4–6, male connector 66 includes a fluid coupling tube 74 and a pair of pin sockets 76a and 76b. Connector 66 is removably connected to female connector 64 in a well known manner. When connectors 64 and 66 are connected together, pins 60 mate with pin sockets 76a and 76b, respectively, and coupling tube 74 mates with rear coupling section 68b of fluid passage 68. The connection of connectors 66, 64 is locked by sliding a locking ring 78 to the position shown in FIG. 4. In a well-known manner, a locking O-ring 80 is urged down into a groove 82 to effect the lock of these couplers.

As shown in FIG. 4, the downstream end of supply line 12 is mounted in male connector 66. Such mounting may be accomplished by any suitable well-known means. Electrical cord 12a contains a pair of electrical wires (not shown). These wires are routed through connection 66 and electrically coupled to pin sockets 76a and 76b, respectively. Compressed air line 12b is coupled to tube 74 via an internal tube or fluid channel (not shown) contained in connector 66. Alternatively, air line 12b may extend through connector 66 and be directly connected to tube 74.

From the above description, it can be understood that a complete electric circuit is established between power source 20 and lamp 56. In addition, a complete fluid path is established between air supply 24 and discharge manifold 40. The compressed air supplied to instrument 10 flows through conduit 62 while lamp 56 is energized. This flow of air greatly aids in the cooling of handle 32 during extended operation of instrument 10 (e.g., exceeding 10–12 minutes). Preliminary tests have suggested that the temperature of handle 32 can be maintained below 80° F. for extended periods of use of instrument 10 (e.g., 10–12 minutes). The air (warmed from heat sink 50) continues from conduit 62, through connector hose 44 and air tube 42, and is discharged out of manifold 40. The same air that aided in the cooling of handle 32 is also forced over reflective surface 38d. The warm air defogs surface 38d and substantially clears surface 38d of water, debris, etc. The forced air also acts as a barrier which, at least in part, may protect surface 38d from tooth debris, dental materials, or aluminum oxide powder from air-abrasion systems.

The weight of instrument 10 is almost the same as a traditional stainless steel handle and mirror. The size (diameter) of handle 32 is far more ergonomically configured than the heavier, smaller diameter stainless steel handle that millions of dental clinicians use daily.

Figure 10:
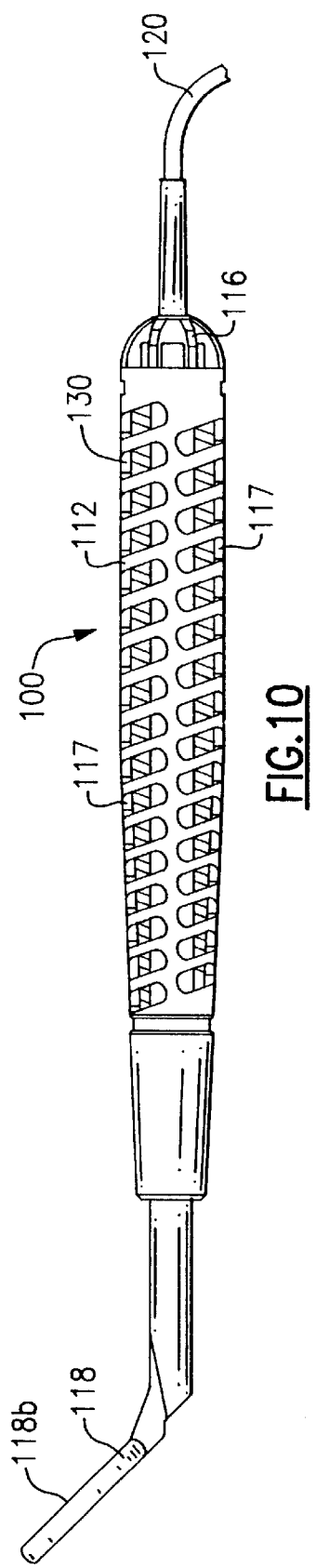
FIG. 10 is a side elevation view of a prior art dental mirror.

A method of retrofitting an existing dental mirror 100, in accordance with the present invention, will now be described with reference to FIG. 10 (prior art) and FIGS. 2–9. As shown in FIG. 10, instrument 100 is essentially constructed as the instrument disclosed in FIG. 1 of Verderber II.

As shown in FIG. 10, instrument 100 comprises a handle 112 containing a plurality of vents 117. A mirror 118, having a reflective surface 118b, is coupled to handle 112. An elongated tubular heat sink 130 is located within handle 112. An electric light source, similar to that shown in FIG. 4 (herein), is contained within heat sink 130. A light transmitting rod (not shown) is located in heat sink 130. An end cap 116 is removably attached to handle 112. Finally, an electrical cord 120 is secured to end cap 116. Cord 120 contains a pair of wires (not shown) coupled to the light source.

The preferred retrofitting method of the present invention comprises the steps of: (a) removing the light source, end cap 116, and electrical cord 120 from handle 112; (b) removing heat sink 130 from handle 112; (c) placing fluid conduit 62 (FIGS. 4 and 7) around heat sink 130; (d) installing the assembly of conduit 62 and heat sink 130 in handle 112; (e) coupling fluid discharge manifold 40 (FIGS. 2 and 3) to fluid conduit 62, via tube 42 and hose 44; (f) attaching support member 46 to the shank of mirror 118 and using member 46 to support manifold 40 adjacent to reflective surface 118b of mirror 118; (g) replacing the light source, end cap 116, and electrical cord 120 with light source 54, male and female quick-disconnect connectors 64, 66, and supply line 12; (h) inserting light source 54 into heat sink 130; (i) attaching connector 64 to handle 112, in place of end cap 116; and (j) connecting connector 66 to connector 64.

Figure 8:
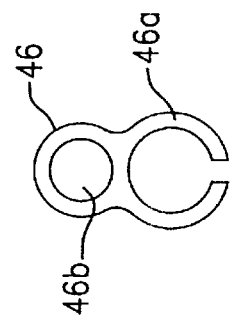
FIG. 8 is an enlarged elevation view of a support member, which is a component of the illuminated dental mirror of FIG. 2.

Referring now to FIGS. 11–13, there is shown a dental mirror instrument 200 employing an elongated protective sheath 202. FIG. 11 shows sheath 202 in an undeployed position; FIG. 12 shows sheath 202 in a partially deployed position; and FIG. 13 shows sheath 202 in a fully deployed position. Instrument 200 is identical to instrument 10, thus the details of its construction will not be presented here. Instrument 200 includes a handle 232. A quick-disconnect coupler 236 is removably attached to the rear end of handle 232. A dental implement, such as a disposable fiber optic mirror 238, is releasably attached to the front end of handle 232, as previously described. Mirror 238 includes a shank 238a. A support member 246, constructed as shown in FIG. 8, is secured to shank 238a of mirror 238.

In the preferred embodiment, protective sheath 202 is an elongated tubular sheath having two open ends 202a and 202b (FIG. 13). End 202a is affixed to support member 246, around the perimeter of member 246, as shown. End 202b remains open and free to allow manual deployment of sheath 202 over and around handle 232 (FIG. 13). In the embodiment shown, instrument 200 also includes a discharge manifold 240, an air tube 242, and a connector hose 244, all constructed and operational as previously described with respect to instrument 10.

In the undeployed position, sheath 202 is rolled up upon itself, from end 202b to end 202a, as shown in FIG. 11. This rolled up configuration facilitates the deployment of sheath 202 over handle 232, because the sheath can simply be unrolled over the handle, as illustrated in FIGS. 12 and 13. Sheath 202 is made from a flexible contaminant-resistant material, such as, for example, Vinyl, Latex, Nitrile or Polyethylene. Once sheath 202 is fully deployed, a protective contaminant-resistant barrier is established from support member 246, over handle 232, to and including coupler 236. In the preferred embodiment, mirror 238, manifold 240, air tube 242, connector hose 244, support member 246, and protective sheath 202 are all disposable items, and are collectively referred to as a disposable assembly 204 (FIG. 11). Thus, after using instrument 200, sheath 202 is rolled back up into its undeployed configuration (FIG. 11), and disposable assembly 204 is discarded. No increase in the temperature of handle 232 was experienced when sheath 202 was fully deployed as shown in FIG. 13.

While the preferred embodiments of the invention have been particularly described in the specification and illustrated in the drawings, it should be understood that the invention is not so limited. Many modifications, equivalents and adaptations of the invention will become apparent to those skilled in the art without departing from the spirit and scope of the invention, as defined in the appended claims.

What I claim is:

1. An illuminated dental mirror instrument, comprising:

a handle defining an interior volume, said handle having front and rear ends;

a disposable mirror containing a reflective surface and including a shank portion releasably attached to the front end of said handle;

an elongated tubular member located within the interior volume of said handle;

an electric light source contained within said elongated tubular member;

means, optically coupled to said light source, for transmitting light emitted from said light source to the front end of said handle;

a thermally conductive fluid conduit, coiled around said elongated tubular member, having an intake end and a discharge end;

a fluid discharge manifold coupled to the discharge end of said fluid conduit via a fluid tube, for fluid communication with said conduit;

support means, removably secured to the shank of said mirror, for supporting said discharge manifold adjacent to the reflective surface of said mirror, the fluid tube being supported by said support means, said manifold being configured to discharge fluid in a fan-like pattern over the reflective surface of said mirror;

a first connector, removably connected to the rear end of said handle, containing a fluid passage removably coupled to the intake end of said fluid conduit for fluid communication with said conduit, said light source being mounted to said first connector;

a second connector, removably connected to and mating with said first connector, containing a fluid passage removably coupled to the fluid passage of said first connector for fluid communication therewith, said second connector including means for conducting electric current, said current conducting means being removably electrically coupled to said light source; and means, coupled to said second connector, for coupling electrical energy and fluid to the current conducting means and fluid passage, respectively, of said second connector.

2. The instrument of claim 1, wherein said first and said second connectors are quick disconnect-connectors.

3. The instrument of claim 1, wherein said elongated tubular member is composed of a thermally conductive material and functions as a heat sink to draw heat away from said light source.

4. The instrument of claim 1, wherein said handle contains a plurality of vents which allow ambient air to circulate in and out of said handle.

5. The instrument of claim 1, wherein said light transmitting means is a light transmission rod, said rod extending into said elongated tubular member and being positioned adjacent to said light source.

6. The instrument of claim 1, wherein the current conducting means of said second connector includes a pair of electrical conductors.

7. The instrument of claim 6, wherein said coupling means includes a pair of electrical wires and a compressed air line all encased in an outer casing, said pair of wires being connected to the pair of electrical conductors of said second connector, said compressed air line being connected to the fluid passage of said second connector.

8. The instrument of claim 7, wherein said coupling means further includes a holder adapted to hold said instrument, said holder having a pair of electrical contacts for coupling an electric power supply to the pair of electrical wires of said coupling means, said holder containing a fluid port for coupling a fluid supply to the compressed air line of said coupling means.

9. An illuminated dental mirror instrument, comprising:

a handle defining an interior volume, said handle having front and rear ends;

a disposable mirror containing a reflective surface and including a shank portion releasably attached to the front end of said handle;

an elongated tubular member located within the interior volume of said handle;

an electric light source contained within said elongated tubular member;

means, optically coupled to said light source, for transmitting light emitted from said light source to the front end of said of handle;

a thermally conductive fluid conduit, coiled around said elongated tubular member, having an intake end and a discharge end;

a fluid discharge manifold coupled to the discharge end of said fluid conduit via a fluid tube, for fluid communication with said conduit;

support means, removably secured to the shank of said mirror, for supporting said discharge manifold adjacent to the reflective surface of said mirror, the fluid tube being supported by said support means, said manifold being configured to discharge fluid in a fan-like pattern over the reflective surface of said mirror;

a first connector, removably connected to the rear end of said handle, containing a fluid passage removably coupled to the intake end of said fluid conduit for fluid communication with said conduit, said light source being mounted to said first connector;

a second connector, removably connected to and mating with said first connector, containing a fluid passage removably coupled to the fluid passage of said first connector for fluid communication therewith, said second connector including means for conducting electric current, said current conducting means being removably electrically coupled to said light source;

means, coupled to said second connector, for coupling electrical energy and fluid to the current conducting means and fluid passage, respectively, of said second connector; and a protective sheath, made from a flexible contaminant resistant material, having a first end secured to said support means and a second end that is open and free to allow manual deployment of said sheath over said handle, whereby a protective contaminant resistant barrier is established over said instrument, from said support means to the rear end of said handle, upon full deployment of said protective sheath.

10. A method of retrofitting a dental mirror instrument of the type including (i) a handle defining an interior volume and containing a plurality of vents, (ii) a mirror with a reflective surface coupled to the handle, (iii) an elongated tubular member located within the interior volume of the handle, (iv) an electric light source contained within the elongated tubular member, (v) means for transmitting light from the light source to the mirror, (vi) an end cap removably attached to the handle, and (vii) an electrical cord, secured to the end cap, including a pair of wires coupled to the light source, said method comprising the steps of:

(a) removing the light source, end cap and electrical cord from the handle;

(b) removing the elongated tubular member from the interior volume of the handle;

(c) placing a thermally conductive, helical-shaped, fluid conduit around the elongated tubular member to create a subassembly, said fluid conduit having an intake end and a discharge end;

(d) installing the subassembly in the interior volume of the handle, such that the discharge end of the fluid conduit is accessible through a vent in the handle;

(e) coupling a fluid discharge manifold to the discharge end of said fluid conduit for fluid communication with said conduit;

(f) attaching a support member to the instrument and using said member to support said discharge manifold adjacent to the reflective surface of the mirror;

(g) replacing the light source, end cap, and electrical cord of said instrument with a replacement light source, first and second connectors, and a supply line, said replacement light source being mounted to said first connector and said supply line being mounted to said second connector;

(h) inserting the replacement light source into the elongated tubular member;

(i) removably connecting the first connector to the handle, in place of the end cap, said first connector containing a fluid passage which is removably coupled to the intake end of said fluid conduit when said first connector is connected to the handle; and (j) removably connecting the second connector to said first connector, said second connector containing a fluid passage which is removably coupled to the fluid passage of said first connector when said second and said first connectors are connected to and mating with each other, said second connector including means for conducting electric current, said current conducting means being removably electrically coupled to said replacement light source when said second connector is connected to and mating with said first connector, and said supply line having a pair of electrical wires coupled to the current conducting means of said second connector and a fluid line coupled to the fluid passage of said second connector.

11. A disposable dental mirror assembly adapted to be removably attached to a handle, said assembly comprising:

a disposable dental mirror including a shank portion and a reflective surface, the shank portion being configured to mate with the handle to which said assembly is to be removably attached;

a disposable support member removably secured to the shank portion of the said dental mirror, said support member containing a support hole therethrough, the support hole being adapted to allow an air tube to pass through and be supported by said support member; and a disposable, elongated protective sheath, made from a flexible contaminant-resistant material, having a first end secured to said support member and a second end, the second end being open and free to allow manual deployment of said sheath over and around the handle to which said assembly is to be removably attached.

12. The disposable dental mirror assembly of claim 11, further comprising an air tube passing through the support hole of said support member and being supported therein.

13. The disposable dental mirror assembly of claim 12, further comprising an air discharge manifold coupled to one end of said air tube, said air tube being supported by said support member such that said manifold is positioned adjacent to the reflective surface of said dental mirror.

* * * * *